US010857149B2

(12) United States Patent
Treppendahl et al.

(10) Patent No.: US 10,857,149 B2
(45) Date of Patent: *Dec. 8, 2020

(54) LIQUID FORMULATIONS OF SALTS OF 1-[2-(2,4-DIMETHYLPHENYLSULFANYL) PHENYL]-PIPERAZINE

(71) Applicant: H. Lundbeck A/S, Valby (DK)

(72) Inventors: Svend Treppendahl, Virum (DK); Heidi Lopez de Diego, Nærum (DK)

(73) Assignee: H. Lundbeck A/S, Valby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/020,799

(22) Filed: Jun. 27, 2018

(65) Prior Publication Data

US 2019/0167667 A1  Jun. 6, 2019

Related U.S. Application Data

(63) Continuation of application No. 15/271,543, filed on Sep. 21, 2016, now Pat. No. 10,034,876, which is a continuation of application No. 14/567,003, filed on Dec. 11, 2014, now Pat. No. 9,475,748, which is a continuation of application No. 13/265,564, filed as application No. PCT/DK2010/050084 on Apr. 16, 2010, now Pat. No. 8,940,746.

(60) Provisional application No. 61/214,540, filed on Apr. 24, 2009.

(30) Foreign Application Priority Data

Apr. 24, 2009 (DK) .................................. 200900531

(51) Int. Cl.
| | | |
|---|---|---|
| A61K 31/495 | (2006.01) | |
| A61K 9/08 | (2006.01) | |
| C07C 59/08 | (2006.01) | |
| C07D 295/096 | (2006.01) | |

(52) U.S. Cl.
CPC .............. *A61K 31/495* (2013.01); *A61K 9/08* (2013.01); *C07C 59/08* (2013.01); *C07D 295/096* (2013.01)

(58) Field of Classification Search
CPC ........ A61K 31/495; A61K 9/08; C07C 59/08; C07C 295/096
See application file for complete search history.

(56) References Cited

U.S. PATENT DOCUMENTS

| | | |
|---|---|---|
| 8,940,746 B2 | 1/2015 | Treppendahl et al. |
| 2006/0089368 A1 | 4/2006 | Puhland et al. |
| 2006/0100242 A1 | 5/2006 | Puschl et al. |
| 2015/0094316 A1 | 4/2015 | Treppendahl et al. |

FOREIGN PATENT DOCUMENTS

| | | |
|---|---|---|
| WO | WO 2003/029232 | 4/2003 |
| WO | WO 2007/144005 | 12/2007 |
| WO | WO 2007/144006 | 12/2007 |
| WO | WO 2008/113358 | 9/2008 |
| WO | WO 2008/113359 | 9/2008 |
| WO | WO 2010/121621 | 10/2010 |

OTHER PUBLICATIONS

Agharkar, et al., "Enhancement of Solubility of Drug Salts by Hydrophilic Counterions: Properties of Organic Salts of an Antimalarial Drug," Journal of Pharmaceutical Sciences, vol. 65, No. 5, May 1976, pp. 747-749.
Berge, et al., "Pharmaceutical Salts", Journal of Pharmaceutical Sciences, vol. 66, No. 1, Jan. 1977, pp. 1-19.
Caira, "Crystalline Polymorphism of Organic Compounds", Topics in Current Chemistry, Springer Verlag Berlin Heidelberg, XP-001156954, vol. 198, 1998, pp. 163-208.
Polymorphism in pharmaceutical solids, Edited by Harvy G. Brittain, Chapter 5, "Generation of Polymorphs, Hydrates, Solvates and Amorphous Solids," by J. Keith Gnillory, 95:183-226 (1999).
Swanepoel, Erna, et. al., "Quality evaluation of generic drugs by dissolution test: changing the USP dissolution medium to distinguish between active and non-active mebendazole polymorphs," European Journal of Pharmaceutics and Biopharmaceutics 55:345-349 (2003).
Glowienke et al., "Structure-activity considerations and in vitro approaches to assess the genotoxicity of 19 methane-, benzene- and toluenesulfonic acid esters," Mutation Research, vol. 581, No. 1-2, Mar. 7, 2005, pp. 23-34.
Verbeeck et al., "Generic substitution: The use of medicinal products containing different salts and implications for safety and efficacy," European Journal of Pharmaceutical Science, vol. 28, No. 1-2, May 2006, pp. 1-6.
Moore et al., "Lu AA12004: a novel potential treatment for mood disorders," Eur. Neuropsychopharmacol, 18, Suppl. 4, S321, 2008, 1 page, Abstract P2b015.
International Search Report and Written Opinion for PCT/DK2010/050084, dated Sep. 20, 2010, 12 pages.
International Preliminary Report on Patentability for PCT/DK2010/050084 dated Oct. 25, 2011; 8 pages.
Non-Final Office Action issued in U.S. Appl. No. 12/527,907 dated Feb. 22, 2012; 21 pages.
Final Office Action issued in U.S. Appl. No. 12/527,907 dated Aug. 21, 2012; 29 pages.
Final Office Action issued in U.S. Appl. No. 12/527,907 dated Feb. 25, 2013; 39 pages.
Nayan Rawal & Associates; Pre-Grant Opposition dated Mar. 30, 2013 filed in corresponding Indian patent Application No. 7699/CHENP/2011 (52 pages).
Advisory Action issued in U.S. Appl. No. 12/527,907 dated Aug. 20, 2013; 3 pages.
Examiner's Answer to Appeal Brief issued in U.S. Appl. No. 12/527,907 dated Feb. 6, 2014; 35 pages.
The Patent Office: Intellectual Property India; Office Action mailed in corresponding Indian patent Application No. 7699/CHENP/2011 dated Aug. 7, 2017 (6 pages).

(Continued)

*Primary Examiner* — Sahar Javanmard
(74) *Attorney, Agent, or Firm* — Fish & Richardson P.C.

(57) ABSTRACT

Liquid formulations of lactic acid addition salts of 1-[2-(2,4-dimethylphenylsulfanyl)-phenyl]piperazine are provided.

10 Claims, 7 Drawing Sheets

(56) References Cited

OTHER PUBLICATIONS

Figure 1:
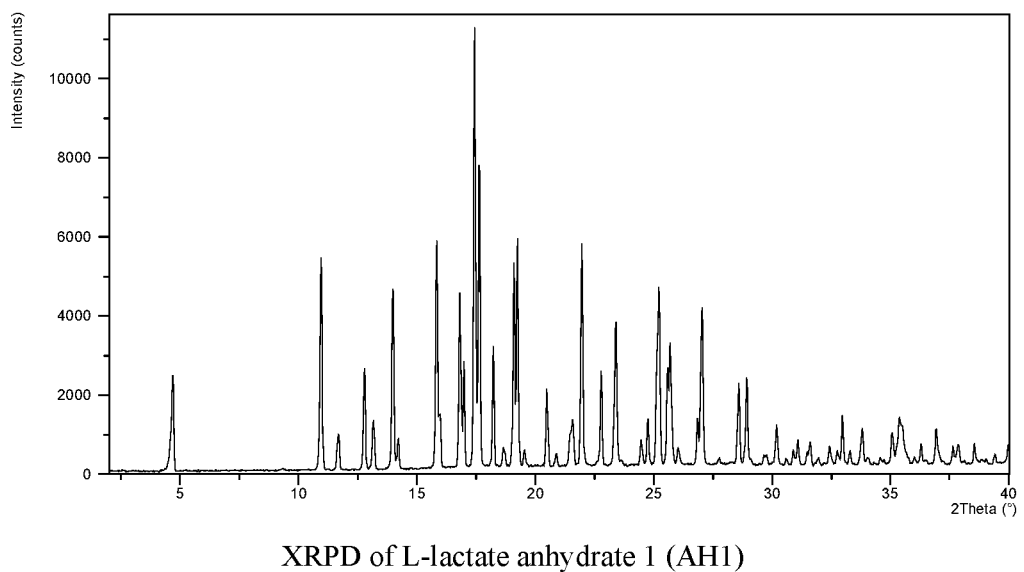

Handbook of Pharmaceutical Salts Properties, Selection and Use, P. Heinrich Stahl, Camille G. Wermuth (Eds.); Publisher: Wiley-VCH; International Union of Pure and Applied Chemistry (IUPAC); Chapter-11, "Selected Procedures for the Preparation of Pharmaceutically Acceptable Salts," pp. 250-263.

XRPD of L-lactate monohydrate 1 (MH1)

XRPD of L-lactate monohydrate 2 (MH2)

XRPD of DL-lactate Alpha form (α)

XRPD of DL-lactate beta form (β)

XRPD of DL-lactate monohydrate (MH), with content of α-form.

XRPD of DL-lactate gamma form (γ), with content of α-form.

LIQUID FORMULATIONS OF SALTS OF 1-[2-(2,4-DIMETHYLPHENYLSULFANYL) PHENYL]-PIPERAZINE

CROSS REFERENCE TO PRIOR APPLICATIONS

This is a continuation of U.S. application Ser. No. 15/271,543, filed Sep. 21, 2016, which is a continuation of U.S. application Ser. No. 14/567,003, filed Dec. 11, 2014, which is a continuation of U.S. application Ser. No. 13/265,564, filed Nov. 1, 2011, now U.S. Pat. No. 8,940,746, which is a U.S. National Phase application under 35 U.S.C. § 371 of International Patent Application No. PCT/DK2010/050084, filed Apr. 16, 2010, which in turn claims the priority of Danish Patent Application No. PA200900531, filed Apr. 24, 2009 and U.S. Provisional Application Ser. No. 61/214,540, filed Apr. 24, 2009, all of which are incorporated by reference herein. The International Application published in English on Oct. 28, 2010 as WO 2010/121621 under PCT Article 21(2).

FIELD OF THE INVENTION

The present invention relates to liquid pharmaceutical formulations of 1-[2-(2,4-dimethylphenylsulfanyl)phenyl] piperazine.

BACKGROUND OF THE INVENTION

The compound 1-[2-(2,4-dimethylphenylsulfanyl)phenyl] piperazine (compound I) has been disclosed in WO 03/029232 as the free base. Compound I has the molecular structure depicted below.

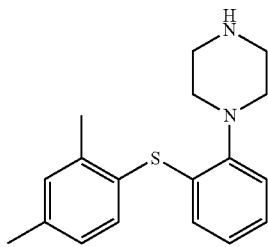 [SMILES: Cc1ccc(Sc2ccccc2N2CCNCC2)c(C)c1]

Different pharmaceutically acceptable acid addition salts of Compound I has been disclosed in WO 2007/144005, including the lactic acid addition salt.

Compound I has been reported to exert serotonin transporter inhibition (WO 03/029232) and is said to be useful for the treatment of affective disorders, e.g. depression and anxiety. In addition, compound I exerts $5$-$HT_3$ antagonism and $5$-$HT_{1A}$ agonism which suggests this compound to be useful e.g. in the treatment of cognitive impairment in depressed patients, and the treatment of pain and residual symptoms in depression (WO 2007/144005 and WO 2008/113359).

In vitro and in vivo experiments conducted with compound I describing receptor efficacy and disease pharmacology have been outlined in WO 03/029232, WO 2007/144005 and WO 2008/113359.

Compound I has been tested in clinical trials in patients using HAM-D (Hamilton Rating Scale for Depression) as clinical end-point; for details see WO 2008/113359. The HAM-D scale may be used to assess the severity of depression in patients by means of a 24 items questionnaire.

According to the outcome of the clinical study compound I is believed to be particularly useful in the treatment of depression avoiding sleep and sexual related adverse events (WO 2008/113359).

For many pharmaceutical compounds, oral administration of a tablet, capsule, pill or similar intended for swallowing is the preferred administration form. However, some patients, e.g. elderly and pediatric patients may have difficulties swallowing, and liquid solutions may be a suitable alternative avoiding the need for swallowing tablets, capsules, pills, etc. A liquid solution further provides a possibility of a flexible dosing regime. In order to limit the volume of a liquid solution it is necessary to have a high concentration of the active ingredient in the solution, which again requires a high solubility of the active ingredient.

The present invention is related to liquid formulations of compound I.

SUMMARY OF THE INVENTION

The present inventors have surprisingly found that the L-lactic acid addition salt (=L-lactate), the D-lactic acid addition salt (=D-lactate) and the DL-lactic acid addition salt (=DL-lactate) of 1-[2-(2,4-dimethylphenylsulfanyl)phenyl] piperazine are highly soluble. Accordingly, the present invention relates to a liquid formulation comprising the L-lactic acid addition salt, the D-lactic acid addition salt and/or the DL-lactic acid addition salt of 1-[2-(2,4-dimethylphenylsulfanyl)phenyl]piperazine.

In one embodiment, the invention relates to a compound which is the L-lactic acid addition salt of 1-[2-(2,4-dimethylphenylsulfanyl)phenyl]piperazine.

In one embodiment, the invention relates to a compound which is the D-lactic acid addition salt of 1-[2-(2,4-dimethylphenylsulfanyl)phenyl]piperazine.

In one embodiment, the invention relates to a method of treatment, said method comprising the administration of a liquid formulation of the present invention to a patient in need thereof.

In one embodiment, the invention relates to the use of a salt of the present invention in the manufacture of a liquid pharmaceutical composition for the treatment of certain diseases.

In one embodiment, the invention relates to a salt of the present invention for use in the treatment of certain diseases, wherein said salts is in a liquid formulation.

In one embodiment, the present invention relates to a container comprising a liquid formulation of the present invention, wherein said container is fitted with a drop aggregate.

FIGURES

FIG. 1: XRPD of L-lactate anhydrate 1 (AH1)
FIG. 2: XRPD of L-lactate monohydrate 1 (MH1)
FIG. 3: XRPD of L-lactate monohydrate 2 (MH2)
FIG. 4: XRPD of DL-lactate alpha form (α)
FIG. 5: XRPD of DL-lactate beta form (β)
FIG. 6: XRPD of DL-lactate monohydrate (MH), with content of α-form
FIG. 7: XRPD of DL-lactate gamma form (γ), with content of α-form

DETAILED DESCRIPTION OF THE INVENTION

The formulations to which the present invention relates are all pharmaceutical compositions.

Characterisation of the crystalline base and the previously known salts of 1-[2-(2,4-dimethylphenylsulfanyl)phenyl]piperazine has been described in WO 2008/113359. The aqueous solubilities of these salts are shown in Table 2. Table 1 shows XRPD reflections, melting points and solubility data of salts of the present invention. As evidenced by the data from Table 1 and 2, the DL-lactic acid addition salt β-form and the L-lactic acid addition salt MH2 have exceptionally high solubilities. Consequently, these salt forms would be suitable for application in liquid formulations comprising 1-[2-(2,4-dimethylphenylsulfanyl)phenyl]piperazine. According to table 2, also the mesylate salt benefits from extremely high solubility. However, use of methane sulfonic acid (mesylate) in combination with alcoholic solvents in the synthesis of pharmaceutical compositions involves a risk of obtaining alkyl mesylate impurities which could be genotoxic (*Mutat. Res.* 581 (2005) 23-34; *Eur. J. Pharm. Sci.* 28 (2006) 1-6). Lactate salts are accordingly superior to mesylate salts for application in pharmaceutical compositions.

For convenience, the L-lactic acid addition salt, the D-lactic acid addition salt and the DL-lactic acid addition salt of 1-[2-(2,4-dimethylphenylsulfanyl)phenyl]piperazine are referred to as salts of the present invention. Both the L-lactic acid addition salt and the DL-lactic acid addition salt exist in several polymorphic forms as shown in the examples. Special mention is made of DL-lactic acid addition salt β form as the salt of the present invention. For the sake of convenience lactic acid addition salts are also referred to as lactates or lactate salts.

The polymorphic forms are characterized by their respective XRPD reflections listed in Table 1 and depicted in FIGS. 1-7.

In the present context the AH1 form of the L-lactate salt is intended to indicate an anhydrate form characterized by XRPD reflections at 4.65, 10.96 and 13.97 (°2θ), and further characterized by FIG. 1.

Figure 2:
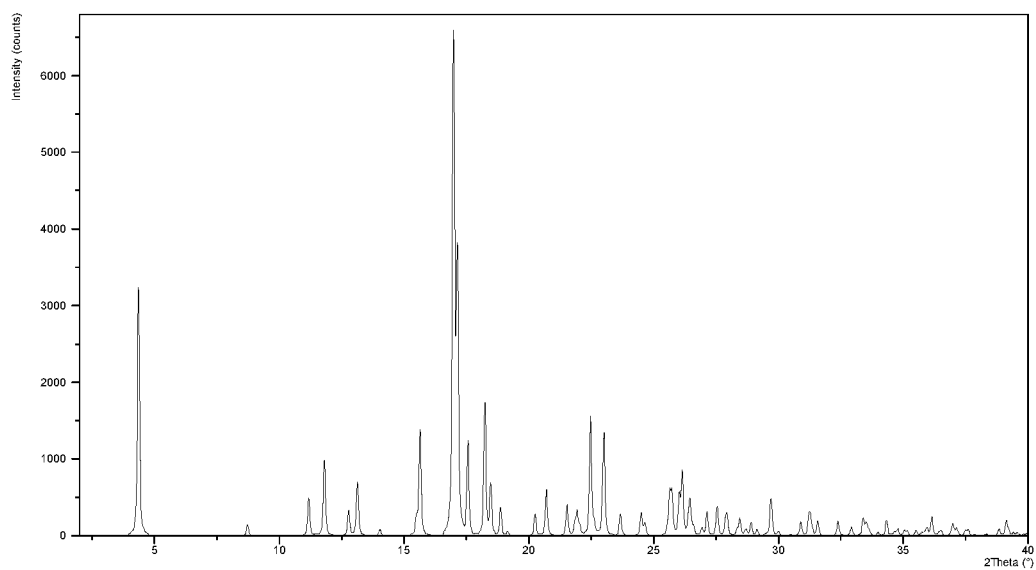

In the present context the MH1 form of the L-lactate salt is intended to indicate a first monohydrate form characterized by XRPD reflections at 4.36, 8.73, 11.18, 11.81, 12.78 and 13.11 (°2θ), and further characterized by FIG. 2.

Figure 3:
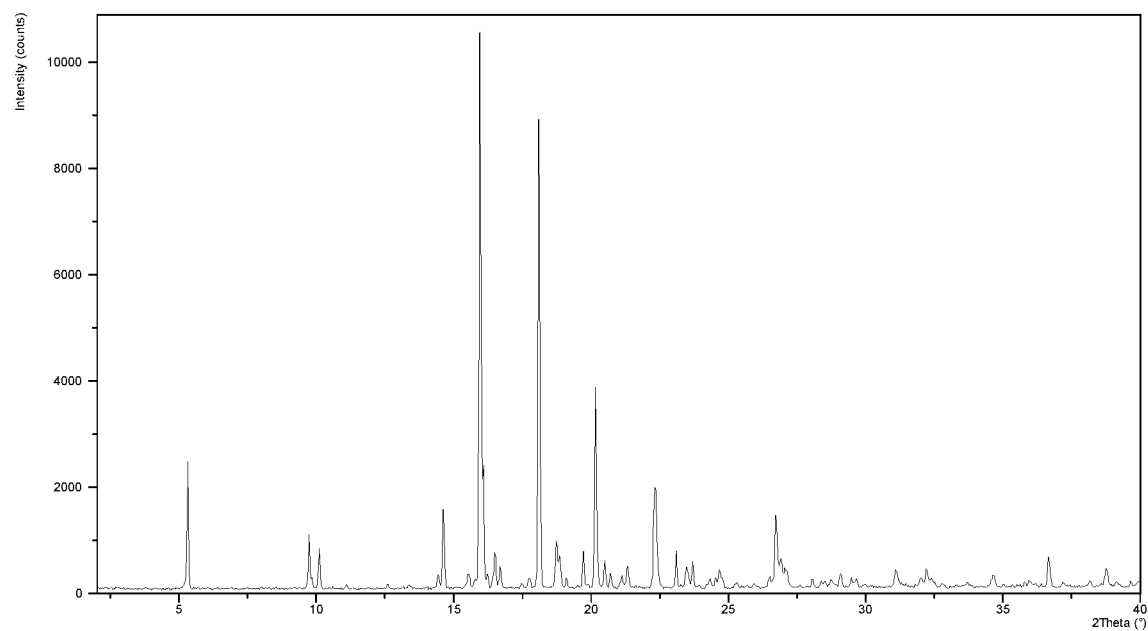

In the present context the MH2 form of the L-lactate salt is intended to indicate a second monohydrate form characterized by XRPD reflections at 5.33, 9.75, 10.10, 14.44 and 14.63 (°2θ), and further characterized by FIG. 3.

Figure 4:
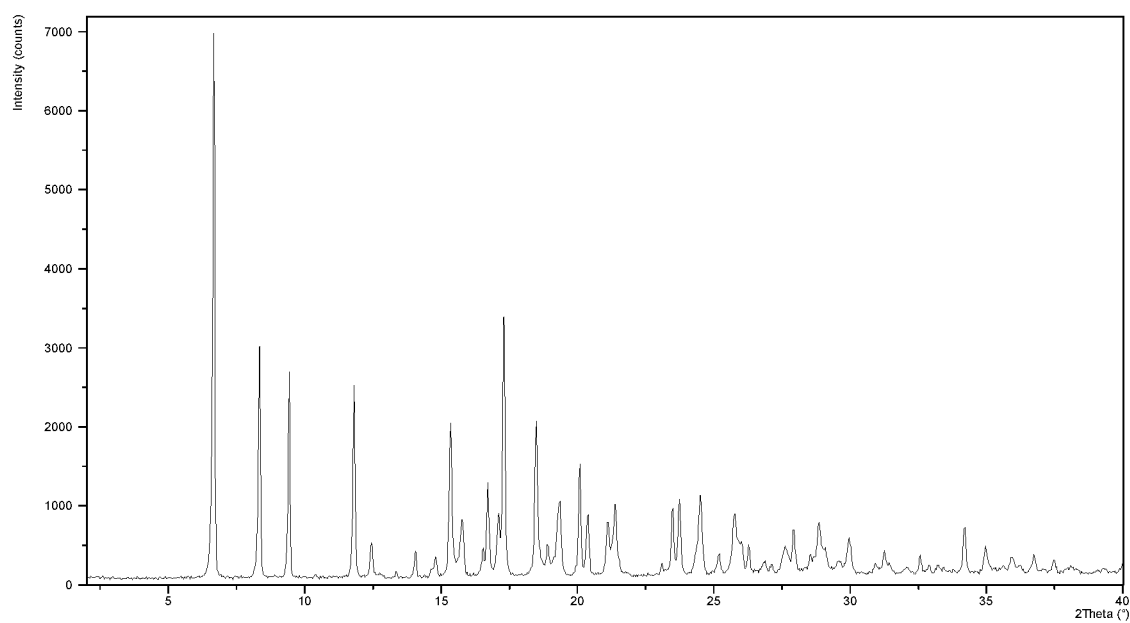

In the present context the α form of the DL-lactate salt is intended to indicate a first polymorph characterized by XRPD reflections at 6.67, 8.33, 9.44, 11.82 and 15.35 (°2θ), and further characterized by FIG. 4.

Figure 5:
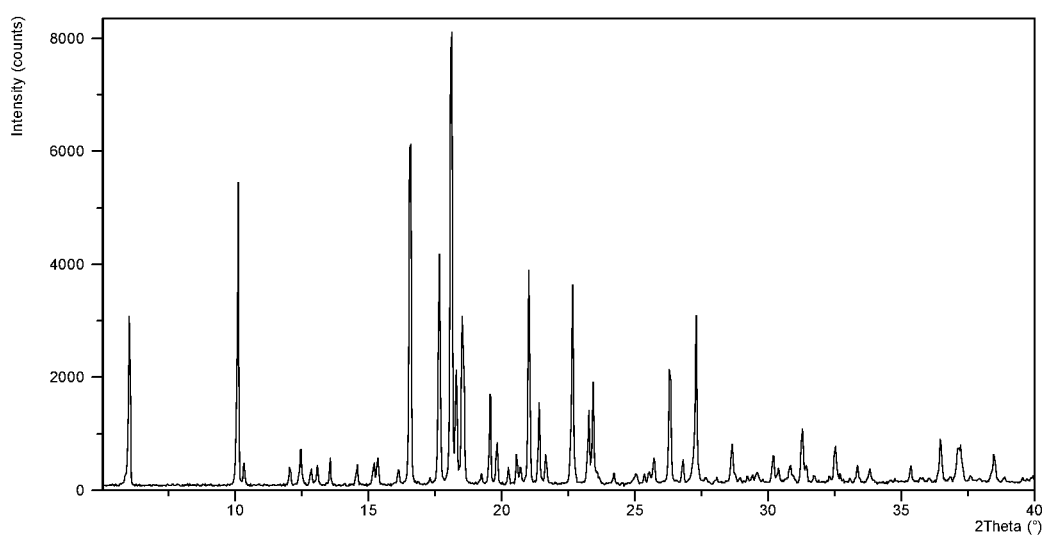

In the present context the β form of the DL-lactate salt is intended to indicate a second polymorph characterized by XRPD reflections at 6.01, 10.10, 10.32, 12.06, 12.84, 13.08 and 13.58 (°2θ), and further characterized by FIG. 5.

Figure 6:
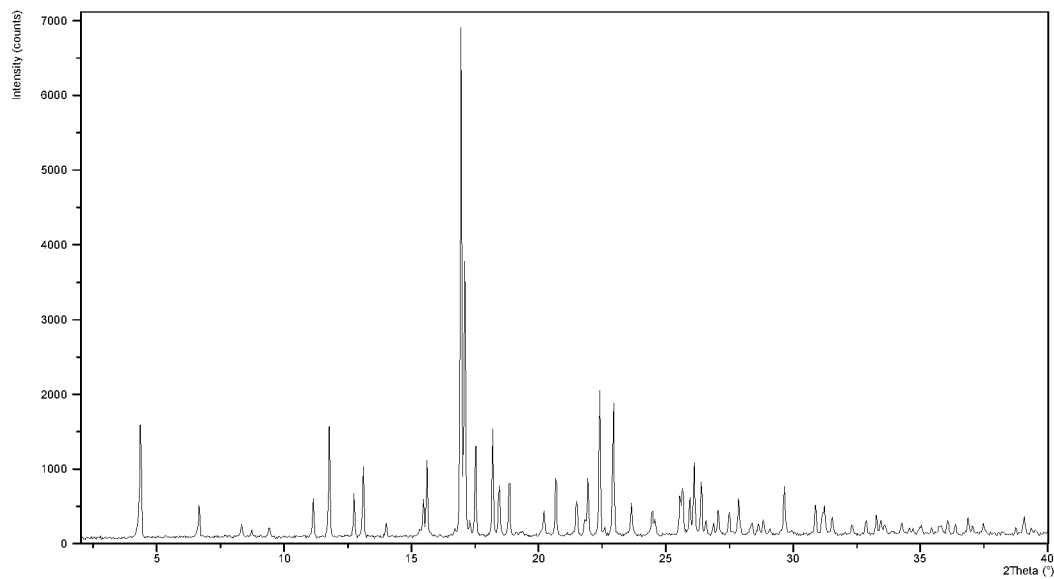

In the present context the MH form of the DL-lactate salt is intended to indicate a monohydrate form characterized by XRPD reflections at 4.37, 8.73, 11.14, 11.78, 12.75 and 13.11 (°2θ), and further characterized by FIG. 6.

Figure 7:
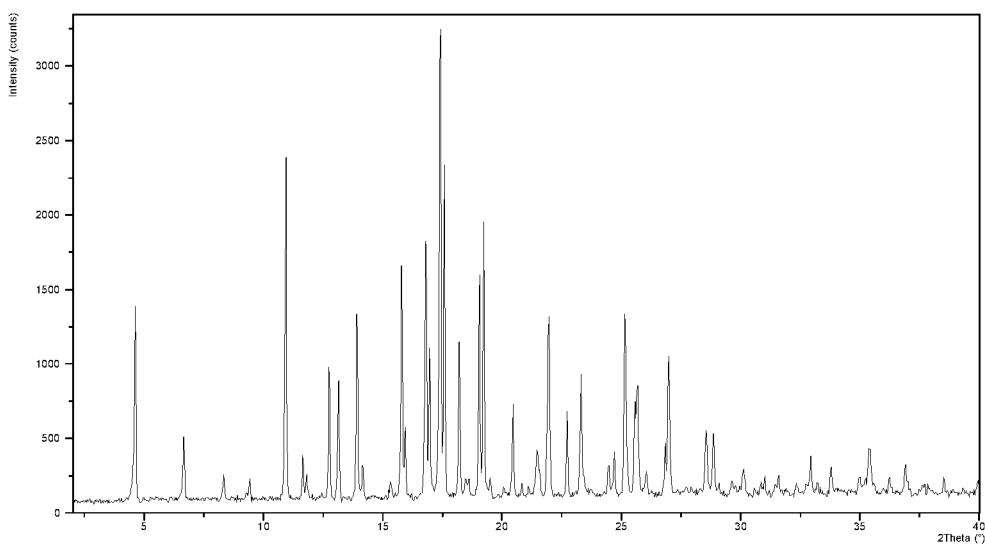

In the present context the γ form of the DL-lactate salt is intended to indicate a third polymorph characterized by XRPD reflections 4.63, 10.94, 11.65 and 13.93 (°2θ), and further characterized by FIG. 7.

Lactic acid is also known as 2-hydroxypropionic acid, and it forms an 1:1 acid addition salt with 1-[2-(2,4-dimethylphenylsulfanyl)phenyl]piperazine which is used in the present invention.

1-[2-(2,4-dimethylphenylsulfanyl)phenyl]piperazine may be prepared as disclosed in WO 03/029232 and WO 2007/144005. The examples disclose specific routes for obtaining the salts of the present invention. In brief, the L-lactate AH1 and the DL-lactate α form may be prepared by addition of L-lactic acid or DL-lactic acid, respectively, to 1-[2-(2,4-dimethylphenylsulfanyl)phenyl]piperazine or vice versa in a suitable anhydrous organic solvent, such as ethyl acetate, followed by precipitation, which precipitation may be brought about by e.g. cooling, removal of solvent, addition of another anhydrous solvent or a combination thereof.

The L-lactate MH1 is formed directly by exposure of L-lactate AH1 to higher relative humidity. The L-lactate MH2 is the more stable form of the L-lactate monohydrates and is formed by adding 1 mL of water to 100 mg of the L-lactate MH1. The aqueous solubility of the L-lactate MH2 is 26 mg/mL. The DL-lactate β form is obtained from a slurry of the DL-lactate α form in water. The β form is the more stable polymorphic modification of the DL-lactate and has a solubility of 8 mg/mL. The DL-lactate MH is obtained by exposure of the DL-lactate α form to high relative humidity. By heating the DL-lactate MH1 the DL-lactate γ form has been obtained. Throughout this document (unless otherwise indicated) an indication of a concentration of a salt of the present invention, e.g. 5 mg/ml, is intended to indicate a concentration equivalent the indicated amount of free base, e.g. 5 mg/ml.

The inventors have noted that the presence of lactic acid in formulations of the present invention increases the solubility of salts of the present invention. The presence of lactic acid, either as D-, L- or DL-lactic acid, may increase the solubility of salts of the present invention to 20-25 mg/mL.

Only salts of L-lactic acid and DL-lactic acid have been made; however 1-[2-(2,4-dimethylphenylsulfanyl)phenyl]piperazine is not chiral, and the L-lactate and the D-lactate are enantiomers, and therefore the D-lactate exists (as mirror image) in the same crystal forms and have the same XRPD-patterns, melting points and solubility as the L-lactate. X-ray powder difractograms (XRPD) for different forms of L-lactate salt and DL-lactate salt are depicted in FIG. 1-7.

Liquid formulations may be intended for oral or parenteral administration. Liquid formulations for parenteral administration including infusion solutions are in many aspects similar to other liquid formulations, but are additionally characterised by being sterile and isotonic.

The liquid oral formulation of the present invention may be presented as a syrup, an elixir, an oral solution, a suspension, or as a concentrated oral formulation. One advantage of these administration forms is that the patient does not have to swallow a solid form, which may be difficult, in particular for elderly and pediatric patients or for patients with traumas in the mouth or throat.

Syrups and elixirs are typically sweetened, flavoured liquids containing an active pharmaceutical ingredient. Syrups typically have higher sugar content, and elixirs often contain alcohol as well. An oral solution is a solution of the active ingredient. A suspension is a two-phase system comprising solid particles dispersed in a liquid. Administration of syrups, elixirs, oral solutions and suspensions typically involves the intake of relatively large amounts of liquid, i.e. 10-50 mL.

In contrast hereto, the concentrated oral formulations of the present invention are administered to the patient by measuring out a pre-determined volume of said formulation from a suitable dispenser, adding the resulting volume to a glass of liquid (water, juice or similar) upon which the patient drinks the liquid. For convenience, the volume measured out is small, e.g. less than 2 mL, such as less than 1 mL, such as less than 0.5 mL. As an example of such product the regulatory authority in the UK, Medicines and Healthcare Products Regulatory Agency (MHRA), has approved a concentrated oral formulation comprising the antidepressant citalopram at 40 mg/ml.

In a particular embodiment, a concentrated oral formulation of the present invention is administered to the patient by measuring out a pre-determined number of drops of said formulation from a suitable dispenser, e.g. a container with a drop aggregate, adding the drops to a glass of liquid (water, juice or similar) upon which the patient drinks the liquid. In this context, a drop aggregate is an aggregate fitted to a container that effects that a liquid inside said container may be dispensed from said container in discrete drops.

Preliminary results have indicated that the concentrated oral formulations of the present invention are prone to being unstable when exposed to light. To overcome this potential problem the formulation can be stored protected from light e.g. in an opaque container or in a container that is light protected by a box.

The concentration of a salt of the present invention in concentrated oral formulations is determined by the number of drops (or the volume) it is desired to collect and the amount of the salts it is desired to administer. It is generally held that measuring out around 5-20 drops is an optimal compromise between safety/efficacy of the treatment on the one hand and convenience on the other. If the concentration of the salts of the present invention is too high, i.e. if only a low number of drops is to be measured out, it may jeopardize safety or efficacy of the treatment. With a low number of drops, one or two drops more or less than desired will significantly increase the uncertainty in the dose provided. On the other hand, if the concentration of the salts of the present invention is too low, the number of drops to be measured out is high, which is inconvenient for the patient or the caretaker.

With daily dosages of 2.5 mg, a concentrated oral formulation with a concentration of 2.5 mg of active ingredient per mL could be appropriate. A concentration of 2.5 mg per mL and a drop number of 20 drops/mL would make it possible to administer 20 drops for a dose of 2.5 mg.

With daily dosages of 2.5 mg, a concentrated oral formulation with a concentration of 5 mg of active ingredient per mL could be appropriate. A concentration of 5 mg per mL and a drop number of 20 drops/mL would make it possible to administer 10 drops for a dose of 2.5 mg.

With daily dosages of 2.5 mg, a concentrated oral formulation with a concentration of 10 mg of active ingredient per mL could be appropriate. A concentration of 10 mg per mL and a drop number of 20 drops/mL would make it possible to administer 5 drops for a dose of 2.5 mg.

With daily dosages of 5 mg, a concentrated oral formulation with a concentration of 5 mg of active ingredient per mL could be appropriate. A concentration of 5 mg per mL and a drop number of 20 drops/mL would make it possible to administer 20 drops for a dose of 5 mg.

With daily dosages of 5 mg, a concentrated oral formulation with a concentration of 10 mg of active ingredient per mL could be appropriate. A concentration of 10 mg per mL and a drop number of 20 drops/mL would make it possible to administer 10 drops for a dose of 5 mg.

With daily dosages of 5 mg, a concentrated oral formulation with a concentration of 20 mg of active ingredient per mL could be appropriate. A concentration of 20 mg per mL and a drop number of 20 drops/mL would make it possible to administer 5 drops for a dose of 5 mg.

With daily dosages of 10 mg, a concentrated oral formulation with a concentration of 10 mg of active ingredient per mL could be appropriate. A concentration of 10 mg per mL and a drop number of 20 drops/mL would make it possible to administer 20 drops for a dose of 10 mg.

With daily dosages of 10 mg, a concentrated oral formulation with a concentration of 20 mg of active ingredient per mL could be appropriate. A concentration of 20 mg per mL and a drop number of 20 drops/mL would make it possible to administer 10 drops for a dose of 10 mg.

With daily dosages of 20 mg, a concentrated oral formulation with a concentration of 20 mg of active ingredient per mL could be appropriate. A concentration of 20 mg per mL and a drop number of 20 drops/mL would make it possible to administer 20 drops for a dose of 20 mg.

Accordingly, in one embodiment a concentrated oral formulations of the present invention comprise approximately 2.5-20 mg/mL of a salt of the present invention. Particular examples include approximately 5-20 mg/mL, approximately 5-15 mg/mL, approximately 5-10 mg/mL, and approximately 2.5, 5, 7.5, 10, 15 or 20 mg/mL.

In one embodiment, a concentrated oral formulation of the present invention comprises at least 2.5 mg/mL of a salt of the present invention.

In one embodiment, a concentrated oral formulation of the present invention comprises at least 5 mg/mL of a salt of the present invention.

In one embodiment, a concentrated oral formulation of the present comprises at least 10 mg/mL of a salt of the present invention.

In one embodiment, a concentrated oral formulation of the present comprises at least 20 mg/mL of a salt of the present invention.

In addition to a salt of the present application, the oral formulation of the present application, and in particular the concentrated oral formulations may comprise solvents, buffers, surfactants, surface tension modifiers, viscosity modifiers, preservatives, antioxidants, colorants, taste maskers, flavours etc.

Examples of solvents include water and other solvents, which are miscible with water or solubilizing agents and suitable for oral purposes. Examples of suitable solvents are ethanol, propylene glycol, glycerol, polyethylene glycols, poloxamers, sorbitol and benzyl alcohol. The aqueous solubility of the active ingredient may further be enhanced by the addition to the solution of a pharmaceutically acceptable co-solvent, a cyclodextrin or a derivative thereof.

A buffer system may be used to maintain the pH of the formulation in an optimal pH-range. A buffer system is a mixture of appropriate amounts of a weak acid such as acetic, phosphoric, succinic, tartaric, lactic or citric acid and its conjugate base. Ideally, the buffer system has sufficient capacity to remain in the intended pH range upon dilution with a neutral, a slightly acidic or a slightly basic beverage.

Surfactants are substances, which solubilize active compounds, which are insufficiently soluble in an aqueous medium, usually with the formation of micelles. Preferably, the surfactant used should be non-ionic due to less toxicity. High concentrations of surfactants may be used to allow for dilution during administration without precipitation. Examples of surfactants include tweens, spans and mono- and diglycerides.

Surface tension modifiers may be included to adjust the drop number for the concentrated oral formulations. An example of a surface tension modifier is ethanol, which decreases the surface tension and increases the drop number.

Viscosity modifiers may be included to adjust the drop velocity for a concentrated oral formulation. The drop velocity for α formulation to be measured out in discrete drops from a container fitted with a drop aggregate should preferably not exceed 2 drops per second. Examples of viscosity modifiers include ethanol, hydroxyethylcellulose, carboxymethylcellulose sodium, methylcellulose, polyvinyl alcohol, polyvinylpyrrolidone, polyethylene glycol and glycerine.

Preservative agents may be added to prevent the growth of micro organisms such as bacteria, yeasts and fungi in liquid formulations, which are likely to be used repeatedly. Suitable preservatives should be pharmaceutically acceptable, physicochemical stable and effective in the desired pH range. Examples of preservative agents include ethanol, benzoic acid, sorbic acid, methylparaben, propylparaben and benzyl alcohol.

A drug substance is typically more sensitive to chemical degradation in dissolved than in solid form; hence it may be necessary to include an antioxidant in the liquid formulation. Examples of antioxidants include propyl gallate, ascorbyl palmitate, ascorbic acid, sodium sulphite, citric acid and EDTA.

Colouring agents may be used in some formulations to introduce a uniformity of appearance to the product. Some active ingredients may further be very sensitive to light and it may prove necessary to add colouring agents to the drop formulations to protect them from light and for the purpose of stabilization. Suitable colouring agents include for example tartrazine and sunset yellow.

Sweetening agents may mask unpleasant taste associated with some formulations or to achieve a desired taste. Examples of sweetening agents are saccharin, sodium salt of saccharin, glucose, sorbitol, glycerol, acesulfame potassium and neohesperidin dihydrochalcon. The taste may be optimized further by the addition of one or more flavouring substances. Suitable flavouring substances are fruit flavours such as cherry, raspberry, black currant, lemon or strawberry flavour or other flavours such as liquorish, anis, peppermint, caramel etc. Particular examples of concentrated oral formulations of lactic acid addition salts of Compound I, which may be administered with a drop aggregate, are listed below. Further examples are provided in the Examples section. By active compound is meant the DL-lactate, the L-lactate or the D-lactate salt of compound I. 1% of the free base form of compound I corresponds to 1.3% of the active compound. 2% of the free base form of compound I corresponds to 2.6% of the active compound. The examples are merely intended to illustrate the invention and should not be construed as limiting 0.33% active compound
0.08% methylparahy droxy benzoate
0.02% propylparahy droxy benzoate
0.2% hydroxyethylcellulose
Water q.s. ad 100%
0.65% active compound
5% hydroxy propyl betacyclodextrin
0.02% propyl gallate
0.2% sorbinsyre
Water q.s. ad 100%
1.3% active compound
0.1% hydroxyethylcellulose
Water q.s. ad 100%
2.6% active compound
10% hydroxyl propyl betacyclodextrin
Water q.s. ad 100%

The pharmacological profile of compound I is disclosed in WO 03/029232, WO 2007/144005 and WO 2008/113359. In brief, compound I is an inhibitor of the serotonin transporter, an antagonist at the 5-HT$_3$ receptor and an agonist at the 5-HT$_{1A}$ receptor. Compound I gives rise to an increase in the extracellular levels of serotonin, noradrenaline, dopamine and acetylcholine in rat brains [Moore et al, *Eur. Neuropsychopharmacol.*, 18, suppl 4, s321, 2008]. The '359 application also discloses the results from clinical trials in depressed patients with the corresponding HBr addition salt which show a surprisingly low level of sleep and sexually related adverse events.

On this background, salts of the present invention are expected to be useful in the treatment of mood disorders, such as major depressive disorder, generalised anxiety disorder, panic disorder, post traumatic stress disorder, and depression associated with anxiety, i.e. co-existing depression and anxiety. The impact on extracellular acetylcholine levels is expected to translate into an effect on cognition, cf. the use of acetylcholine esterase inhibitors in the treatment of Alzheimer's disease. Thus, the salts of the present invention may also be used in the treatment of depression associated with cognitive impairment and Alzheimer's disease.

A fraction of patients with major depressive disorder will respond to treatment with e.g. a selective serotonin transport inhibitor in the sense that they will improve on clinically relevant scales, such as HAMD or MADRS, but where other symptoms, such as cognitive and/or sleep symptoms remain. In the present context, these patients are referred to as suffering form depression with residual symptoms. The salts of the present invention are expected to be useful in the treatment of such patients.

Pre-clinical data presented e.g. in WO 2008/113359 supports the notion that compound I may be used in the treatment of pain. In one embodiment, pain is or pain is associated with chronic pain including phantom limb pain, neuropathic pain, diabetic neuropathy, post-herpetic neuralgia (PHN), carpal tunnel syndrome (CTS), HIV neuropathy, complex regional pain syndrome (CPRS), trigeminus neuralgia, tic douloureux, surgical intervention (e.g. post-operative analgesics), diabetic vasculopathy, capillary resistance, diabetic symptoms associated with insulitis, pain associated with menstruation, pain associated with cancer, dental pain, headache, migraine, tension-type headache, trigeminal neuralgia, temporomandibular joint syndrome, myofascial pain, muscular injury, fibromyalgia syndrome, bone and joint pain (osteoarthritis), rheumatoid arthritis, rheumatoid arthritis and edema resulting from trauma associated with burns, strains or fracture bone pain due to osteoarthritis, osteoporosis, bone metastases or unknown reasons, gout, fibrositis, myofascial pain, thoracic outlet syndromes, upper back pain or lower back pain (wherein the back pain results from systematic, regional, or primary spine disease (radiculopathy), pelvic pain, cardiac chest pain, non-cardiac chest pain, spinal cord injury (SCI)-associated pain, central post-stroke pain, cancer neuropathy, AIDS pain, sickle cell pain or geriatric pain. In one embodiment, pain is irritable bowl syndrome (IBS).

On the basis of the pharmacological profile, it is also expected that the salts of the present invention may be useful in the treatment of eating disorders, such as obesity, binge eating, anorexia and bulimia nervosa, and substance abuse, such as alcohol, nicotine and drug abuse.

Hence, in one embodiment, the invention relates to a method of treating a disease selected from mood disorders; major depressive disorder; general anxiety disorder; panic disorder; post traumatic stress disorder; depression associated with cognitive impairments, Alzheimer's disease or anxiety; depression with residual symptoms; chronic pain; eating disorder or abuse said method comprising the administration of a therapeutically effective amount of a liquid formulation of the present invention to a patient in need thereof.

Due to the very low level of adverse events observed in treatment with 1-[2-(2,4-dimethylphenylsulfanyl)phenyl] piperazine, a liquid formulation of the present invention may also be useful as second line treatment for patients who cannot use other drugs, such as other anti-depressants, such as selective serotonin reuptake inhibitors (SSRI), selective noradrenalin reuptake inhibitors (NRI), noradrenaline/serotonin reuptake inhibitors (SNRI) or tri-cyclics (TCA) due to sleep or sexually related adverse events. In this embodiment, the patient to be treated has received another medication (or is still receiving it), which medication was ceased or reduced (or has to be ceased or reduced) due to sleep or sexually related adverse events. In one embodiment, said liquid formulation is a concentrated oral formulation.

In one embodiment, the patient to be treated has been diagnosed with the disease said patient is being treated for.

A typical oral dosage is in the range of from about 0.01 to about 5 mg/kg body weight per day, preferably from about 0.01 to about 1 mg/kg body weight per day, administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

A typical oral dosage for adults is in the range of 0.5-50 mg/day of a salt of the present invention, such as 1-10 mg/day. This may typically be achieved by the administration of 0.5-50 mg, such as 0.5, 1, 2.5, 5, 10, 15, 20 25, 30 or 40 mg of a salt of the present invention once or twice daily. In case of pediatric treatment, the dose may be reduced according to age and/or body weight.

A "therapeutically effective amount" of a compound as used herein means an amount sufficient to cure, alleviate or partially arrest the clinical manifestations of a given disease and its complications in a therapeutic intervention comprising the administration of said compound. An amount adequate to accomplish this is defined as "therapeutically effective amount". The term also includes amounts sufficient to cure, alleviate or partially arrest the clinical manifestations of a given disease and its complications in a treatment comprising the administration of said compound. Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. Nonetheless, prophylactic (preventive) and therapeutic (curative) treatment are two separate aspect of the invention. The patient to be treated is preferably a mammal, in particular a human being.

In one embodiment, the invention relates to the use of a salt of the present invention for the manufacture of a liquid formulation for the treatment of a disease selected from mood disorders; major depressive disorder; general anxiety disorder; panic disorder; post traumatic stress disorder; depression associated with cognitive deficits, Alzheimer's disease or anxiety; depression with residual symptoms; chronic pain; eating disorder or abuse.

In one embodiment, said salt is chosen from the β form of the DL-lactate salt and the MH2 form of the L-lactate salt.

In one embodiment, said liquid formulation is a concentrated oral formulation.

In one embodiment, the present invention relates to a salt of the present invention for use in the treatment of a disease selected from mood disorders; major depressive disorder; general anxiety disorder; panic disorder; post traumatic stress disorder; depression associated with cognitive deficits, Alzheimer's disease or anxiety; depression with residual symptoms; chronic pain; eating disorder or abuse, wherein said salt is in a liquid formulation.

In one embodiment, said salt is chosen from the DL-lactate salt and the L-lactate salt.

In one embodiment, said liquid formulation is a concentrated oral formulation.

In one embodiment the present invention relates to a liquid formulation comprising a salt of 1-[2-(2,4-dimethylphenylsulfanyl)phenyl]piperazine selected from the DL-lactic acid addition salt, the L-lactic acid addition salt and/or the D-lactic acid addition salt. In particular, said liquid formulation is a concentrated oral formulation.

In one embodiment the present invention relates to a compound which is the L-lactic acid addition salt of 1-[2-(2,4-dimethylphenylsulfanyl)phenyl]piperazine. Particular mention is made of the MH2 form.

In one embodiment the present invention relates to a compound which is the L-lactic acid addition salt of 1-[2-(2,4-dimethylphenylsulfanyl)phenyl]piperazine with XRPD reflections at approximately 5.33, 9.75, 10.10, 14.44 and 14.63 (°2θ) e.g. with an XRPD pattern as depicted in FIG. 3.

In one embodiment the present invention relates to a compound which is the D-lactic acid addition salt of 1-[2-(2,4-dimethylphenylsulfanyl)phenyl]piperazine.

In one embodiment the present invention relates to a compound which is the β form of the DL-lactic acid addition salt with XRPD reflections at approximately 6.01, 10.10, 10.32, 12.06, 12.84, 13.08, 13.58 (°2θ), e.g. with a XRPD pattern as depicted in FIG. 5.

The salts of the present invention may be administered either alone or in combination with another therapeutically active compound, wherein the two compounds may be administered either simultaneously or sequentially. Examples of therapeutically active compounds which may advantageously be combined with salts of the present invention include sedatives or hypnotics, such as benzodiazepines; anticonvulsants, such as lamotrigine, valproic acid, topiramate, gabapentin, carbamazepine; mood stabilizers such as lithium; dopaminergic drugs, such as dopamine agonists and L-Dopa; drugs to treat ADHD, such as atomoxetine; psychostimulants, such as modafinil, ketamine, methylphenidate and amphetamine; other antidepressants, such as mirtazapine, mianserin and buproprion; hormones, such as T3, estrogen, DHEA and testosterone; atypical antipsychotics, such as olanzapine and aripiprazole; typical antipsychotics, such as haloperidol; drugs to treat Alzheimer's diseases, such as cholinesterase inhibitors and memantine, folate; S-Adenosyl-Methionine; immunmodulators, such as interferons; opiates, such as buprenorphins; angiotensin II receptor 1 antagonists (ATI antagonists); ACE inhibitors; statins; and alpha1 adrenergic antagonist, such as prazosin.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

Unless otherwise indicated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

EXAMPLES

Analysis

X-Ray powder diffractograms (XRPD) were measured on a PANalytical X'Pert PRO X-Ray Diffractometer using $CuK_{\alpha 1}$ radiation. The samples were measured in reflection mode in the 2θ-range 5-40° C. using an X'celerator detector. Throughout this document, diffraction data are indicated ±0.1 (°2θ).

Example 1. AH1 Form of 1-[2-(2,4-dimethyl-phenylsulfanyl)-phenyl] Piperazine, L-Lactate 1-[2-(2,4-Dimethyl-phenylsulfanyl)-phenyl]-piperazine base (5.00 g) was dissolved in ethyl acetate (50 mL) at 50° C. The solution was a little turbid and was filtered through a paper filter. L-(+)-lactic acid (1.84 g) was added to the solution and stirred at room temperature. Precipitation started and the suspension was stirred at room temperature for two hours and the product was isolated by filtration. The solid was dried in the vacuum oven at 40° C. over night. It was not possible to measure the aqueous solubility of the AH1 as the substance transforms into monohydrate when exposed to water.

Example 2. MH1 Form of 1-[2-(2,4-dimethyl-phenylsulfanyl)-phenyl] Piperazine, L-Lactate 100 mg of AH1 form of 1-[2-(2,4-dimethyl-phenylsulfanyl)-phenyl] piperazine, L-lactate from example 1 was left in an open container at ambient conditions (22° C., 30% RH). It was not possible to measure solubility of the MH1, as the compound transforms into the MH2 in aqueous slurry.

Example 3. MH2 Form of 1-[2-(2,4-dimethyl-phenylsulfanyl)-phenyl] Piperazine, L-Lactate To 100 mg of MH1 form of 1-[2-(2,4-dimethyl-phenylsulfanyl)-phenyl] piperazine, L-lactate from example 2 was added 1 mL of water, and the mixture was left overnight. The precipitate (MH2-form) is filtered of.

Example 4. α form of 1-[2-(2,4-dimethyl-phenylsulfanyl)-phenyl] piperazine, DL-Lactate 1-[2-(2,4-Dimethyl-phenylsulfanyl)-phenyl]-piperazine base (5.00 g) was dissolved in ethyl acetate (50 mL) at 50° C. The solution was a little turbid and was filtered through a paper filter and became clear. DL-lactic acid (1.68 g) was added to the solution and stirred at room temperature. Precipitation started after two hours. The suspension was stirred at room temperature for two hours and the product isolated by filtration. The solid was dried in the vacuum oven at 40° C. over night. It was not possible to measure the solubility of the α form in water, as the compound transformed into the β form in the aqueous slurry.

Example 5. β Form of 1-[2-(2,4-dimethyl-phenylsulfanyl)-phenyl] Piperazine, DL-Lactate 100 mg of α form of 1-[2-(2,4-dimethyl-phenylsulfanyl)-phenyl] piperazine, DL-lactate from example 5 was added 1 mL of water, and the mixture is left overnight. The precipitate (β-form) was filtered of.

Example 6. MH Form of 1-[2-(2,4-dimethyl-phenylsulfanyl)-phenyl] Piperazine, DL-Lactate 10 mg of α form of 1-[2-(2,4-dimethyl-phenylsulfanyl)-phenyl] piperazine, DL-lactate from example 5 was exposed to high relative humidity (25° C., 95% RH) for 4 h. It was not possible to measure solubility of MH in water because it transformed into the beta form in aqueous slurry.

Example 7. γ Form of 1-[2-(2,4-dimethyl-phenylsulfanyl)-phenyl] Piperazine, DL-Lactate 10 mg of MH form of 1-[2-(2,4-dimethyl-phenylsulfanyl)-phenyl] piperazine, DL-lactate from example 7 was heated to 50° C. It was not possible to measure aqueous solubility of the γ form because it transforms into the beta form in aqueous slurry.

Example 8. β form of 1-[2-(2,4-dimethyl-phenylsulfanyl)-phenyl] Piperazine, DL-Lactate 200 g of 1-[2-(2,4-dimethyl-phenylsulfanyl)-phenyl] piperazine, HBr (526 mmol) was stirred in Me-THF (3.5 L) and 1 M NaOH (1 L) were added. The suspension was stirred for 15 minutes after which all solids were dissolved. The phases were separated, and after blank filtration the Me-THF phase was reduced to half volume. After cooling to room temperature DL-lactic acid (1.5 eq~789 mmol) was added and the solution was seeded with 0.5% of the J form. After 5 minutes, the precipitation starts and the suspension was left stirring at ambient temperature overnight. The suspension was then cooled on ice, filtered and washed with 200 mL Me-THF and dried overnight under vacuum at 50° C.

TABLE 1

Summary of selected reflection for the XRPD patterns, melting point and room temperature solubility of the forms of 1-[2-(2,4-dimethyl-phenylsulfanyl)-phenyl] piperazine, lactate

| Salt | Crystal Form | Selected XRPD reflections (°2θ) | Melting point (° C.) | Solubility (mg base/mL) |
|---|---|---|---|---|
| L-lactate | AH1 | 4.65, 10.96, 13.97 | ~140 | Na |
| L-lactate | MH1 | 4.36, 8.73, 11.18, 11.81, 12.78, 13.11 | na | na (>26) |
| L-lactate | MH2 | 5.33, 9.75, 10.10, 14.44, 14.63 | na | 26 (pH = 5.2) |
| DL-lactate | α | 6.67, 8.33, 9.44, 11.82, 15.35 | ~119 | na |
| DL-lactate | β | 6.01, 10.10, 10.32, 12.06, 12.84, 13.08, 13.58 | ~149 | 8 (pH = 6) |
| DL-lactate | MH | 4.37, 8.73, 11.14, 11.78, 12.75, 13.11 | na | na |
| DL-lactate | γ | 4.63, 10.94, 11.65, 13.93 | ~123 | na | na = non applicable

TABLE 2

Room temperature solubility of previously known salt forms of 1-[2-(2,4-dimethyl-phenylsulfanyl)-phenyl] piperazine

| Salt | Solubility (mg base/mL) |
|---|---|
| Crystalline base | 0.1 |
| HBr, α-form | 2.0 |
| HBr, β-form | 1.2 |
| HCl | 3.0 |
| HCl, MH | 2.0 |
| Fumarate | 0.4 |
| Maleate | ~1 |
| Meso-tartrate | ~0.7 |
| L-(+)-tartrate | ~0.4 |
| D-(-)-tartrate | ~0.4 |
| Sulphate | ~0.1 |
| Phosphate | ~1 |
| Nitrate | ~0.8 |
| Mesylate | >45 |

Example 9. Synthesis of 1-[2-(2,4-dimethylphenylsulfanyl)phenyl] Piperazine D,L-Lactate Salt

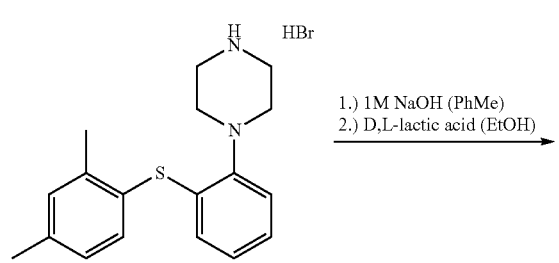

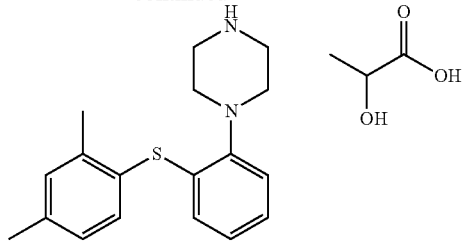

50 g (132 mmol) of the HBr salt was suspended in 800 mL toluene and 250 mL (250 mmol; 1.9 eq) 1M aq. NaOH was added. The two-phase mixture was warmed to 65° C. until all solid has gone into solution and then cooled to room temperature. The phases were separated, and the organic phase was evaporated in vacuo to give a slightly yellow solid. 125 mL ethanol and 20 mL (269 mmol; 2.0 eq) DL-lactic acid (90%) were added, and the suspension was warmed until all solids were dissolved, followed by cooling to room temperature. The solution was seeded with a few crystals of 1-[2-(2,4-dimethylphenylsulfanyl)phenyl]piperazine D,L-lactate β form, and the suspension was stirred over night at room temperature and subsequently cooled with an ice-bath. The precipitate was filtered-off and washed with ethanol, dried in vacuum oven to give 36.5 g 1-[2-(2,4-dimethylphenylsulfanyl)phenyl]piperazine D,L-lactate β form (71% yield).

Example 10. Concentrated Oral Formulations

The concentrated oral formulations indicated below were prepared and exposed to stability testing under conditions as indicated. 25/60 indicates 25° C. and 60% RH, 40/75 indicates 40° C. and 75% RH, and 60 indicates 60° C. The numbers indicate the amount of residual active compound following the test period.

The residual amount of 1-[2-(2,4-dimethylphenylsulfanyl)phenyl]piperazine in the oral drop formulations was determined by gradient reverse-phase HPLC. The mobile phase consisted of a mixture of water and acetonitrile with TFA added. Detection was by UV at 226 nm.

a)
1.3% active compound~1% free base
0.08% methylparahydroxybenzoate
0.02% propylparahydroxybenzoate
Water q.s. ad 100%

| Time (months:) | 25/60 mg/ml | 40/75 mg/ml | 60 mg/ml |
|---|---|---|---|
| 0 | 10.6 | 10.6 | 10.6 |
| ½ | 10.6 | 10.4 | 10.4 |
| 1 | 10.4 | 10.5 | 10.4 |
| 2 | 10.1 | 10.1 | 10.2 |
| 3 | 9.8 | 9.8 | 9.9 | b)
1.3% active compound~1% free base
5% hydroxy propyl betacyclodextrin
Water q.s. ad 100%

| Time (months:) | 25/60 mg/ml | 40/75 mg/ml | 60 mg/ml |
|---|---|---|---|
| 0 | 10.4 | 10.4 | 10.4 |
| ½ | 10.3 | 10.3 | 10.3 |

| Time (months:) | 25/60 mg/ml | 40/75 mg/ml | 60 mg/ml |
|---|---|---|---|
| 1 | 10.4 | 10.4 | 10.4 |
| 2 | 9.9 | 10.1 | 10.2 |
| 3 | 9.7 | 9.5 | 9.8 | c)
1.3% active compound~1% free base
0.1% hydroxyethylcellulose
Water q.s. ad 100%

| Time (months:) | 25/60 mg/ml | 40/75 mg/ml | 60 mg/ml |
|---|---|---|---|
| 0 | 10.4 | 10.4 | 10.4 |
| ½ | 10.5 | 10.6 | 10.5 |
| 1 | 10.4 | 10.5 | 10.5 |
| 2 | 10.1 | 10.2 | 10.1 |
| 3 | 9.6 | 9.5 | 9.6 | d)
1.3% active compound~1% free base
1.1% L-lactic acid
0.1% hydroxyethylcellulose
Water q.s. ad 100%

| Time (months:) | 25/60 mg/ml | 40/75 mg/ml | 60 mg/ml |
|---|---|---|---|
| 0 | 10.5 | 10.5 | 10.5 |
| ½ | 10.5 | 10.7 | 10.5 |
| 1 | 9.7 | 9.8 | 9.8 |
| 2 | 10.4 | 10.4 | 10.3 |
| 3 | 10.1 | 10.1 | 10.1 |
| 6 | 9.8 | 9.8 | 9.8 | e)
2.6% active compound~2% free base
10% hydroxy propyl betacyclodextrin
Water q.s. ad 100%

| Time (months:) | 25/60 mg/ml | 40/75 mg/ml | 60 mg/ml |
|---|---|---|---|
| 0 | 20.6 | 20.6 | 20.6 |
| ½ | 20.7 | 20.6 | 20.8 |
| 1 | 19.9 | 18.9 | 19.6 |
| 2 | 21.1 | 21.0 | 20.9 |
| 3 | 20.2 | 20.8 | 20.7 |
| 6 | | 19.7 | 20.1 | f)
2.6% active compound~2% free base
10% hydroxy propyl betacyclodextrin
10% ethanol 96%
Water q.s. ad 100%

| Time (months:) | 25/60 mg/ml | 40/75 mg/ml | 60 mg/ml |
|---|---|---|---|
| 0 | 20.8 | 20.8 | 20.8 |
| ½ | 20.9 | 20.7 | 21.1 |
| 1 | 19.7 | 19.8 | 19.7 |
| 2 | 21.0 | 20.9 | 20.8 |
| 3 | 20.7 | 20.6 | 20.9 |
| 6 | | 19.9 | 20.0 | g)
2.6% active compound~2% free base
10% methyl betacyclodextrin
Water q.s. ad 100%

| Time (months:) | 25/60 mg/ml | 40/75 mg/ml | 60 mg/ml |
|---|---|---|---|
| 0 | 20.8 | 20.8 | 20.8 |
| ½ | 19.6 | 19.3 | 19.6 |
| 1 | 21.0 | 20.4 | 20.6 |
| 2 | 20.0 | 20.5 | 20.2 |
| 3 | 20.8 | 21.1 | 21.0 |
| 6 | 20.3 | 19.9 | 19.6 | h)
2.6% active compound~2% free base
10% methyl betacyclodextrin
10% ethanol 96%
Water q.s. ad 100%

| Time (months:) | 25/60 mg/ml | 40/75 mg/ml | 60 mg/ml |
|---|---|---|---|
| 0 | 21.0 | 21.0 | 21.0 |
| ½ | 19.7 | 20.2 | 19.8 |
| 1 | 20.7 | 20.9 | 20.8 |
| 2 | 20.2 | 20.7 | 20.4 |
| 3 | 21.3 | 21.2 | 21.0 |
| 6 | 20.3 | 20.5 | 20.0 |

The invention claimed is:

1. A liquid pharmaceutical formulation prepared from:
a salt of 1-[2-(2,4-dimethylphenylsulfanyl)phenyl]piperazine, the salt being selected from the group consisting of a β form of a DL-lactic acid addition salt, an MH2 form of a L-lactic acid addition salt and an MH2 form of a D-lactic acid addition salt; and
water.

2. The formulation of claim 1, wherein the salt is the β form of the DL-lactic acid addition salt.

3. The formulation of claim 1, wherein the salt is the MH2 form of the L-lactic acid addition salt.

4. The formulation of claim 1, wherein the salt is the MH2 form of the D-Lactic acid addition salt.

5. The formulation of claim 1, wherein the concentration of the salt is at least 2.5 mg/mL.

6. A container fitted with a drop aggregate, which container comprises the formulation of claim 1.

7. The container of claim 6, wherein the salt is the form of the DL-lactic acid addition salt.

8. The container of claim 6, wherein the salt is the MH2 form of the L-lactic acid addition salt.

9. The container of claim 6, wherein the salt is the MH2 form of the D-Lactic acid addition salt.

10. The container of claim 6, wherein the concentration of the salt is at least 2.5 mg/mL.

* * * * *

UNITED STATES PATENT AND TRADEMARK OFFICE
CERTIFICATE OF CORRECTION

Page 1 of 1

PATENT NO.         : 10,857,149 B2
APPLICATION NO.    : 16/020799
DATED              : December 8, 2020
INVENTOR(S)        : Svend Treppendahl and Heidi Lopez de Diego It is certified that error appears in the above-identified patent and that said Letters Patent is hereby corrected as shown below:

In the Claims

Column 16, Line 57:
In Claim 7, delete "the form" insert -- the β form -- therefor.

Signed and Sealed this
Sixteenth Day of February, 2021

Drew Hirshfeld
*Performing the Functions and Duties of the
Under Secretary of Commerce for Intellectual Property and
Director of the United States Patent and Trademark Office*